(12) United States Patent
Buchbinder et al.

(10) Patent No.: US 11,926,800 B2
(45) Date of Patent: Mar. 12, 2024

(54) REGENERATION OF A DEHYDROGENATION CATALYST SLIP-STREAM

(71) Applicant: UOP LLC, Des Plaines, IL (US)

(72) Inventors: Avram M. Buchbinder, Chicago, IL (US); John J. Senetar, Naperville, IL (US); Wei Pan, Hoffman Estates, IL (US); Wolfgang A Spieker, Glenview, IL (US); Richard A. Johnson, II, Algonquin, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 17/574,439

(22) Filed: Jan. 12, 2022

(65) Prior Publication Data
US 2022/0135887 A1    May 5, 2022

Related U.S. Application Data

(60) Provisional application No. 63/282,461, filed on Nov. 23, 2021.

(51) Int. Cl.
*C10G 35/09* (2006.01)
*B01J 23/96* (2006.01)
*B01J 38/02* (2006.01)

(52) U.S. Cl.
CPC .............. *C10G 35/09* (2013.01); *B01J 23/96* (2013.01); *B01J 38/02* (2013.01); *C10G 2300/1085* (2013.01); *C10G 2400/20* (2013.01)

(58) Field of Classification Search
CPC .......... C01G 35/09; B01J 23/96; B01J 38/02; C10G 2300/1085; C10G 2400/20
See application file for complete search history.

(56) References Cited

U.S. PATENT DOCUMENTS

| | | | |
|---|---|---|---|
| 9,834,496 B2 | 12/2017 | Pretz et al. | |
| 10,065,905 B2 | 9/2018 | Pretz et al. | |
| 10,227,271 B2 | 3/2019 | Pretz | |
| 10,392,319 B2 | 8/2019 | Pretz et al. | |
| 10,590,048 B2 | 3/2020 | Pretz | |
| 2004/0065591 A1 | 4/2004 | Rockwell | |
| 2015/0004093 A1 | 1/2015 | Zhou et al. | |
| 2015/0202615 A1 | 7/2015 | Zhou et al. | |
| 2021/0002186 A1* | 1/2021 | Iaccino | C07C 5/321 |
| 2022/0135887 A1 | 5/2022 | Buchbinder et al. | |

FOREIGN PATENT DOCUMENTS

GB          748777 A  *  5/1956

OTHER PUBLICATIONS

PCT Search Report and Written Opinion, PCT/US 22/80134, dated Mar. 10, 2023.

\* cited by examiner

*Primary Examiner* — Coris Fung
*Assistant Examiner* — Catriona M Corallo
(74) *Attorney, Agent, or Firm* — Paschall & Associates, LLC; James C. Paschall (57) ABSTRACT

A fluidized catalytic reactor system cycles from 0.05-5% of catalyst at a time through a rejuvenation unit to be heated in the presence of oxygen to maintain catalyst activity. The use of the rejuvenation unit that may be 2% of the size of the main catalyst regeneration unit allows for reduction in equipment size and in catalyst inventory. The catalyst that is sent to the rejuvenation unit may be spent catalyst but may be partially or fully regenerated catalyst. The rejuvenation unit may be heated by combusting fuel or by hot flue gas.

15 Claims, 6 Drawing Sheets

REGENERATION OF A DEHYDROGENATION CATALYST SLIP-STREAM

This application claims priority to provisional patent application Ser. No. 63/282,461, filed Nov. 23, 2021, which is incorporated herein in its entirety.

FIELD

The field is the reaction of a feed with a fluidized catalyst. The field may particularly relate to reacting a paraffin feed with a fluidized dehydrogenation catalyst.

BACKGROUND

Light olefin production is vital to the production of sufficient plastics to meet worldwide demand. Paraffin dehydrogenation (PDH) is a process in which light paraffins such as ethane and propane can be dehydrogenated to make ethylene and propylene, respectively. Dehydrogenation is an endothermic reaction which requires external heat to drive the reaction to completion.

Dehydrogenation catalysts may incorporate a dehydrogenation metal and a metal oxide support. The catalyst must be sufficiently robust and appropriately sized to be able to resist the attrition expected in a fluidized bed system.

In PDH reactions with fluidized catalyst, coke can deposit on the catalyst while catalyzing the reaction, and the dehydrogenation metals may be deactivated by extended contact with reaction conditions. The catalyst may be regenerated in a catalyst regenerator by combusting coke from the catalyst in the presence of oxygen. The hot regenerated catalyst may then be transferred back to the reactor to catalyze the reaction. If insufficient heat is provided to drive the endothermic reaction, olefin production can suffer. For Pt—Ga catalyst used in the prior-art, to maintain the catalyst activity, regeneration of catalyst has been accomplished by burning supplemental fuel and then subjugating the carbon-burned catalyst to additional oxygen treatment for more than 2 minutes in each cycle to maintain catalyst activity over time. However, exposing catalyst to a treatment gas for longer than two minutes necessitates large vessels and high volumes of air flow. Smaller vessel sizes are preferable for cost, but the residence time resulting in smaller vessels may be insufficient to maintain activity over thousands of cycles necessary in commercial operation.

There is a need, therefore, for improved methods of regenerating the catalyst to reduce the size of regeneration vessels and reduce the volume of air flow needed.

BRIEF SUMMARY

A fluidized catalytic reactor is used in which the catalyst is continuously cycled through the dehydrogenation reactor with short regeneration cycles while additionally separating a slip-stream of spent catalyst from the reactor for rejuvenation. By rejuvenating a small slip stream of catalyst for a long period of time, the vessel size needed for regeneration and volume of air flow can be significantly reduced compared to prior art processes.

The deactivation of the catalyst that accumulates over many cycles is fully or at least mostly reversible by treatment in oxygen-containing gas for extended periods of time, even if the cycles during which the catalyst deactivated over time involved only shorter regeneration time.

DETAILED DESCRIPTION

We have discovered a process and apparatus for providing a reactor with an active catalyst and maintaining catalyst activity for thousands of cycles, while minimizing the vessel size needed for regeneration and volume of air needed for regeneration. In this process, there is continuous cycling of most of the catalyst through the dehydrogenation reactor and regenerator, with short regeneration cycles while additionally separating a slipstream of spent catalyst for rejuvenation. By treating a small slip stream of catalyst for a long period of time, the vessel size needed for regeneration and volume of air flow can be reduced relative to processes in prior art. There are two surprising aspects of this process. The first is that deactivation of a platinum and gallium containing catalyst that accumulates over many cycles is fully or at least mostly reversible by treatment in oxygen-containing gas for extended period of time, even if the cycles during which the catalyst deactivated over time involved only shorter regeneration time. Thus, rejuvenation has been found to be necessary only about every 2000 cycles and thus only about 0.05% in quantity of the catalyst needs to be diverted to rejuvenation in each pass or cycle. A vessel that rejuvenates 0.05% in quantity of the catalyst stream for 40 minutes only needs to contain less than 4% of the amount in quantity of catalyst contained in the main regenerator if the main regenerator has a catalyst residence time of 2 minutes, and thus results in smaller vessels. This reduces equipment size and catalyst inventory compared to having a large main regenerator to provide more contact time to regenerate the catalyst in every pass. A further feature of this process is that treatment with oxygen does not need to occur in a sequential step but can occur concurrently with coke and fuel burning, even in the same vessel. The water generated from coke and fuel burning does not further deactivate catalyst. Thus, a rejuvenation step can be accomplished on spent catalyst rather than on regenerated or partially regenerated catalyst and can occur in the presence of water and carbon dioxide, allowing the catalyst to be heated by combusting fuel or by hot flue gas and still be rejuvenated provided contact time is sufficient. In some embodiments, the heating of catalyst in the slip-steam does not use direct contact with burning supplemental fuel. Instead, the heat can be provided by a heated O2-containing gas stream passing through the slip steam or by indirect heating methods. The process involves transferring less than 5% and as little as in quantity of the spent catalyst (from the reactor) to a rejuvenation zone in which the catalyst is heated to >700° C. (preferably >715° C., more preferably >735° C., optimally >750° C.) in the presence of O2 (>2% O2, preferably about 20% O2) for longer than 5 minutes (preferably longer than 20 minutes, more preferably longer than 40 minutes). As increased oxygen exposure requires less time for rejuvenation, one may also consider the use of oxygen enriched air beyond 20% O2. Some methods to implement this invention are fluidizing a slip stream of spent catalyst with air in a vessel containing heating tubes, or another means which indirectly heats the catalyst. An alternative method is to transfer some heat to the catalyst using hot air which is heated by exchanging heat with the hot regeneration flue gas, or by heating the air by another means such as an electric heater or a fired heater. Another alternative is that the catalyst in the slip stream is heated by exchanging heat with the main regenerator. Catalyst is maintained in the vessel for an average residence time of greater than 5 minutes, preferably greater than 20 minutes and more preferably greater than 40 minutes. The treated catalyst is returned to the reactor or regenerator. Another method involves fluidizing a slip stream of spent catalyst with air and fuel to directly heat the catalyst, maintaining catalyst in the vessel for an average residence time of greater than 5 minutes, and then returning the treated catalyst to the reactor or regenerator. Another aspect of the invention may involve lifting a slip stream of spent catalyst to a zone or vessel above the regenerator and treating the catalyst with a portion of the hot regenerator flue gas for an average residence time of greater than 5 minutes. A slip stream of regenerated or partially regenerated hot catalyst may be diverted from the top of the regenerator combustion zone to a vessel or pipe while maintaining the catalyst in the vessel for an average residence time of greater than 5 minutes. The average number of cycles between rejuvenations for the average catalyst particle may be 200-4000 cycles, 1000-4000 cycles or 1500-3000 cycles. The average amount of time between rejuvenations for the average catalyst particle may be 50-700 hours or preferably 260-525 hours. The time in the rejuvenator may be 5-120 minutes, 5-60 minutes and preferably 20-60 minutes. The temperature of the catalyst in the rejuvenator may be 715-790° C. and preferably 740-770° C. The amount of catalyst in rejuvenator as a fraction of total catalyst inventory is about 0.1%-5% in quantity. The amount of catalyst in rejuvenator as a fraction of catalyst in the regenerator is about 0.2%-6% in quantity. If preheated air or flue gas is used to heat the catalyst, the temperature of the gas at the inlet of the rejuvenator is about 850-1000° C. and preferably about 875-950° C. If preheated air or flue gas is used to heat the catalyst, the weight ratio of gas to catalyst is about 0.5-1.5 kg/kg. The fluidization velocity in the rejuvenator is about 1.5-3.5 ft/s. The overall catalyst flow rate to rejuvenator as fraction of catalyst circulation rate is 0.03%-2%, or preferably 0.05%-0.5%. The rejuvenator may contain cyclones, filters or other means to minimize catalyst exiting the vessel with the gas used for heating.

The rejuvenation process can be a batch process where catalyst is loaded into a vessel and heated. In this case additional time is needed to provide time to heat the catalyst. The rejuvenation process can alternatively be a continuous process. If rejuvenation is a continuous process, then the catalyst flow rate to the rejuvenator is defined as the catalyst mass flow to the rejuvenator per unit time. If rejuvenation is a batch process, then the catalyst flow rate to the rejuvenator is defined as the average mass of catalyst per batch divided by the batch time contact time. The teachings herein may be applicable to any process that requires catalyst to be regenerated to provide heat to drive an endothermic catalytic reaction, such as paraffin dehydrogenation (PDH) or fluidized bed catalytic naphtha reforming. PDH catalyst is used in a dehydrogenation reaction process to catalyze the dehydrogenation of paraffins, such as ethane, propane, iso-butane, and n-butane, to olefins, such as ethylene, propylene, isobutene and n-butenes, respectively. The PDH process will be described exemplarily to illustrate the disclosed apparatus and process. An analogous catalytic reforming process may include the catalyst rejuvenation system described herein.

The conditions in the dehydrogenation reactor may include a temperature of about 500 to about 800° C., a pressure of about 40 to about 310 kPa and a catalyst to feed ratio of about 5 to about 100. The dehydrogenation reaction may be conducted in a fluidized manner such that gas, which may comprise the reactant paraffins with or without a fluidizing inert gas, is distributed to the reactor in a way that lifts the dehydrogenation catalyst in the reactor vessel while catalyzing the dehydrogenation of paraffins. During the catalytic dehydrogenation reaction, coke is deposited on the dehydrogenation catalyst leading to reduction of the activity of the catalyst. The dehydrogenation catalyst must then be regenerated.

Figure 1:
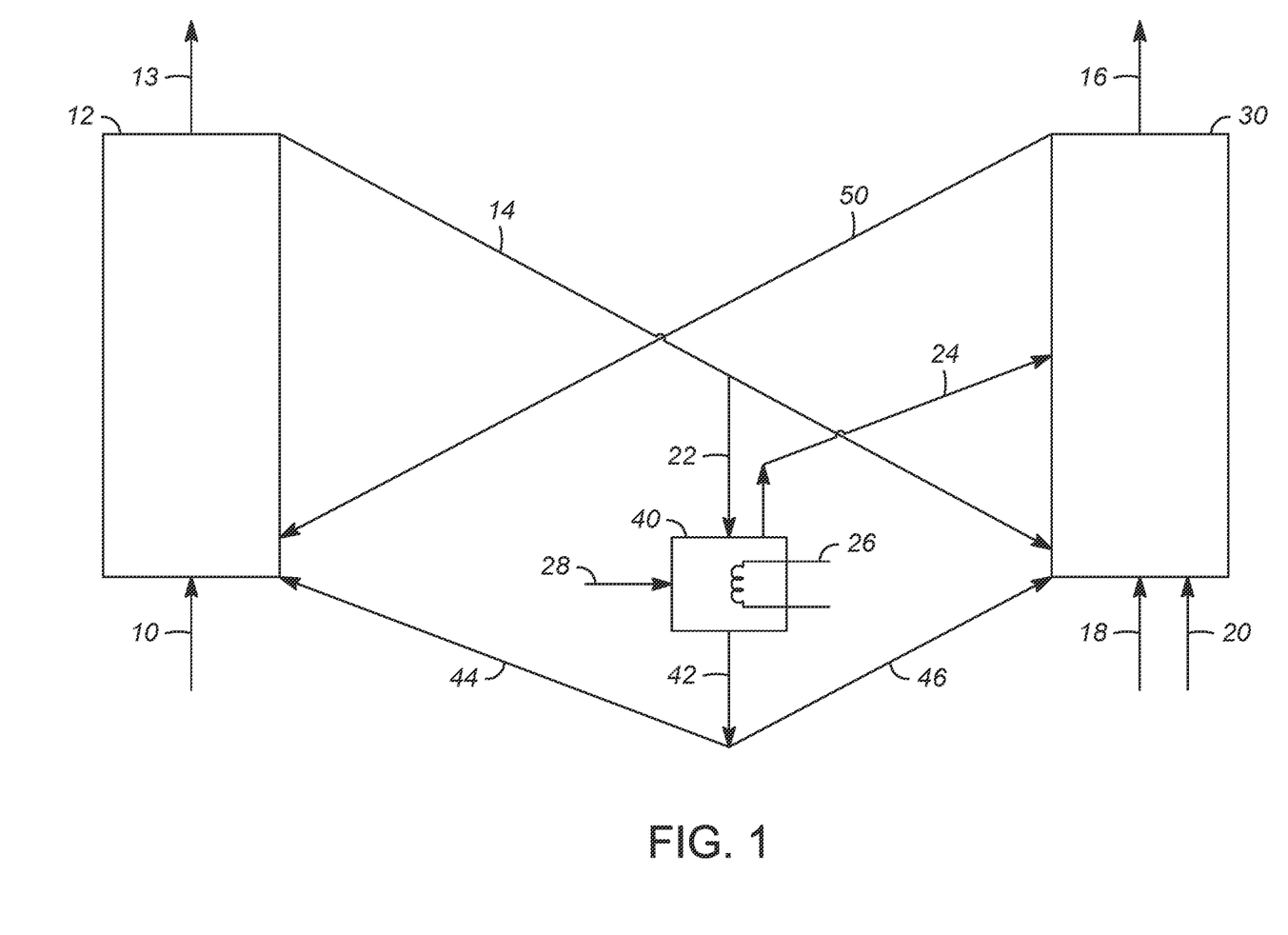
FIG. 1 is a schematic drawing of a process and apparatus of the present disclosure.

A PDH reactor 12 is shown in FIG. 1. A feed line 10 may deliver a reactant stream of feed to the reactor 12. The reactant stream may predominantly comprise propane or butane, but other paraffins such as ethane may be present in the reactant stream in conjunction with or to the exclusion of other paraffins. Any feed distributor can distribute the reactant stream to the reactor 12. A product stream 13 such as a mixture of propylene and hydrogen exits a top portion of reactor 12. Spent catalyst stream 14 is removed from the reactor 12 and sent to the bottom of regenerator unit 30. A small portion 22 (about 0.05-5% in quantity) of spent catalyst 14 is removed and sent to a catalyst rejuvenator unit 40 which may be heated by indirect heater 26. An air stream 28 is shown to provide oxygen to catalyst rejuvenator unit 40. A flue gas stream 24 may be sent from regenerator 30 to rejuvenator unit 40 for indirect heating of the rejuvenator unit 40. The rejuvenated catalyst 42 exits the bottom of rejuvenator 40 and either returns to reactor 12 through pipe 44 or is sent to regenerator 30 through pipe 46. In connection with regenerator 30 is shown a regeneration flue gas 16 exiting out the top, a regeneration gas stream 18 and a fuel stream 20 such as a fuel gas entering the bottom of regenerator 30. Regenerated catalyst stream 50 is returned to reactor 12 from regenerator unit 30.

Figure 2:
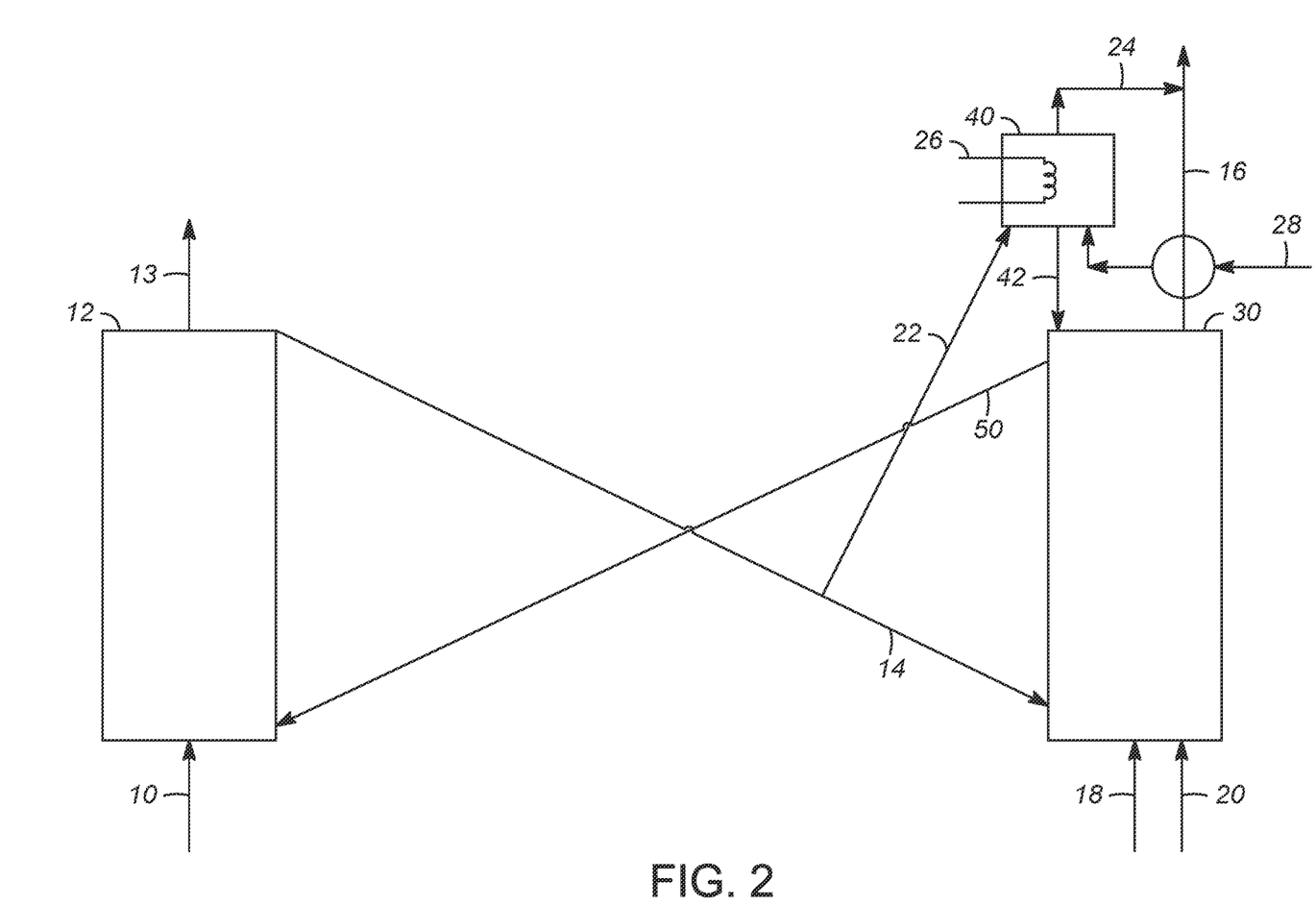
FIG. 2 is a schematic drawing of a process and apparatus of an alternative embodiment of the present disclosure.

FIG. 2 shows a variation of FIG. 1 where the rejuvenator unit is located above regenerator unit 30. A PDH reactor 12 is shown in FIG. 2. A feed line 10 may deliver a reactant stream of feed to the reactor 12. The reactant stream may predominantly comprise propane or butane, but other paraffins such as ethane may be present in the reactant stream in conjunction with or to the exclusion of other paraffins. Any suitable feed distributor can distribute the reactant stream to the reactor 12. A product stream 13 such as a mixture of propylene and hydrogen exits a top portion of reactor 12. Spent catalyst stream 14 is removed from the reactor 12 and sent to the bottom of regenerator unit 30. A small portion 22 (about 0.05-5% in quantity) of spent catalyst 14 is removed and sent to a catalyst rejuvenator unit 40 which may be heated by indirect heater 26. An air stream 28 is shown to provide oxygen to catalyst rejuvenator unit 40. A flue gas stream 24 is shown to provide indirect heating of rejuvenator 40 and is combined with flue gas stream 16. The rejuvenated catalyst 42 exits the bottom of rejuvenator 40 and is sent to regenerator 30. In connection with regenerator 30 is shown, a regeneration gas stream such as air 18 and a fuel stream 20 (if necessary) such as a fuel gas entering the bottom of regenerator 30. Regenerated catalyst stream 50 is returned to reactor 12 from regenerator unit 30.

Figure 3:
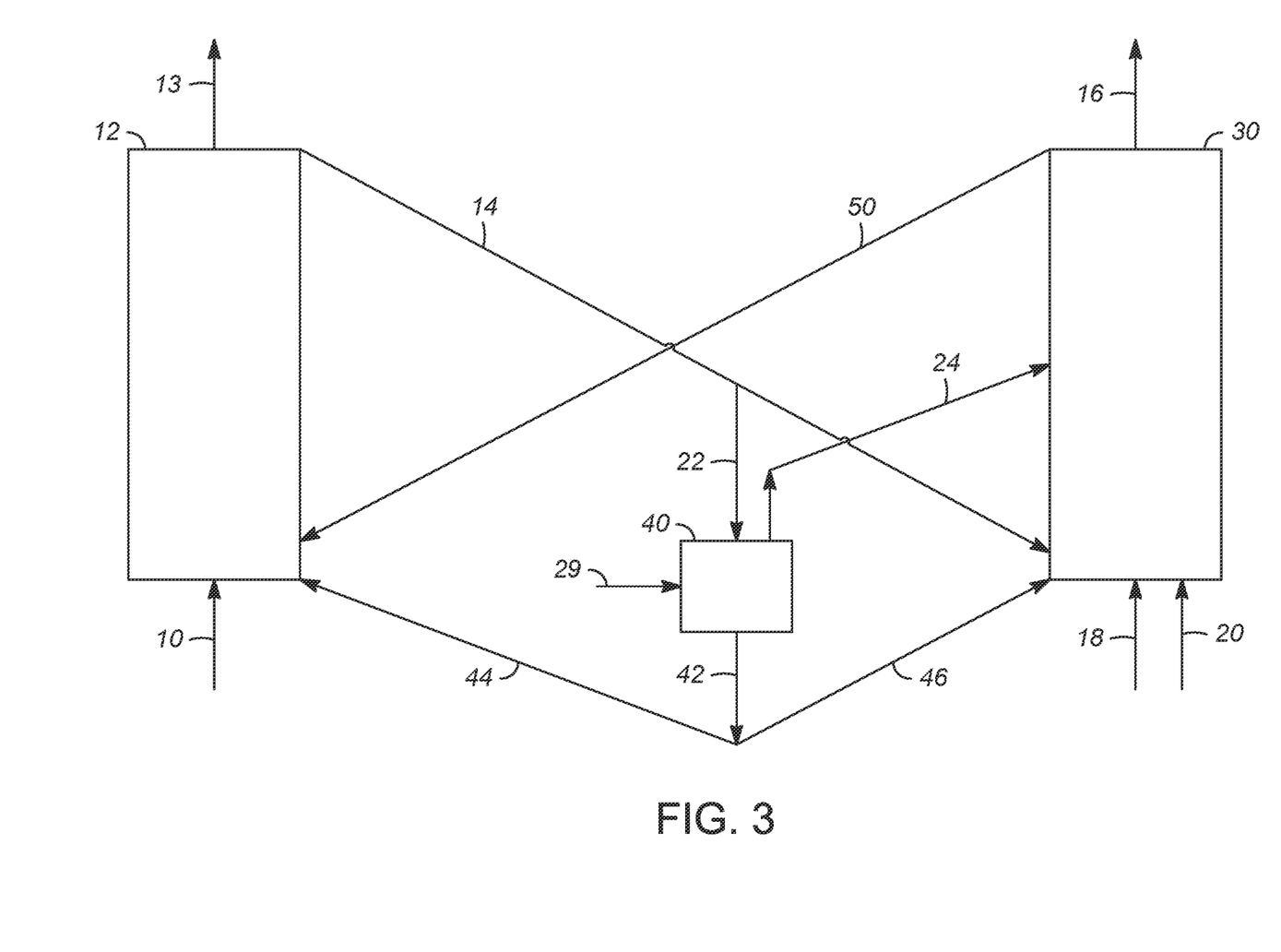
FIG. 3 shows a schematic drawing of a process and apparatus in which an air and fuel mixture is sent directly to a catalyst rejuvenator.

In another embodiment, an air and fuel mixture is sent to the catalyst rejuvenator instead of using indirect heating. A reactor 12 is shown in FIG. 3. A feed line 10 may deliver a reactant stream of feed such as propane to the reactor 12. The reactant stream may predominantly comprise propane or butane, but other paraffins such as ethane may be present in the reactant stream in conjunction with or to the exclusion of other paraffins. Any suitable feed distributor can distribute the reactant stream to the reactor 12. A product stream 13 such as a mixture of propylene and hydrogen exits a top portion of reactor 12. Spent catalyst stream 14 is removed from the reactor 12 and sent to the bottom of regenerator unit 30. A small portion 22 (about 0.05-5% in quantity) of spent catalyst 14 is removed and sent to a catalyst rejuvenator unit 40 which may be heated by heat produced by a mixture of air and fuel entering through line 29. A flue gas stream 24 may be sent to regenerator 30 from rejuvenator unit 40. The rejuvenated catalyst 42 exits the bottom of rejuvenator 40 and either returns to reactor 12 through pipe 44 or is sent to regenerator 30 through pipe 46. In connection with regenerator 30 is shown a regeneration flue gas 16 exiting out the top, a regeneration gas stream 18 and a fuel stream 20 such as a fuel gas entering the bottom of regenerator 30. Regenerated catalyst stream 50 is returned to reactor 12 from regenerator unit 30.

Figure 4:
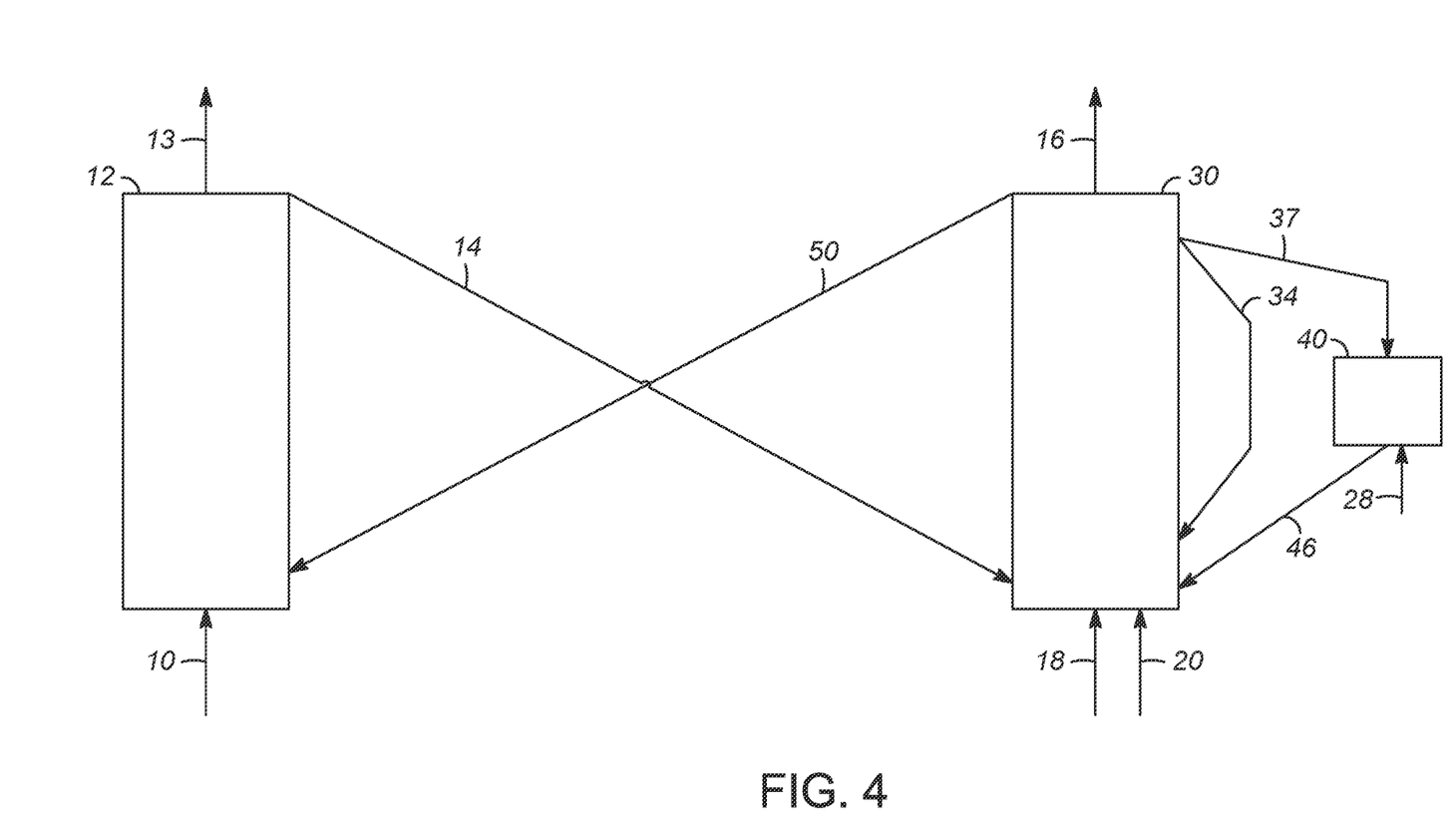
FIG. 4 is a schematic drawing of a process and apparatus of an alternative embodiment of the present disclosure.

FIG. 4 shows a PDH reactor 12. A feed line 10 may deliver a reactant stream of feed to reactor 12. The reactant stream may predominantly comprise propane or butane, but other paraffins such as ethane may be present in the reactant stream in conjunction with or to the exclusion of other paraffins. Any feed distributor can distribute the reactant stream to the reactor 12. A product stream 13 such as a mixture of propylene and hydrogen exits a top portion of reactor 12. Spent catalyst stream 14 is removed from the reactor 12 and sent to the bottom of regenerator unit 30. A small portion 32 (about 0.05-5% in quantity) of spent catalyst is removed from regenerator 30 and sent to a catalyst rejuvenator unit 40. An air stream 28 is shown to provide oxygen to catalyst rejuvenator unit 40. The rejuvenated catalyst 42 exits the bottom of rejuvenator 40 and is sent to regenerator 30 through pipe 46. In connection with regenerator 30 is shown a regeneration flue gas 16 exiting out the top, a regeneration gas stream 18 and a fuel stream 20 such as a fuel gas entering the bottom of regenerator 30. Regenerated catalyst stream 50 is returned to reactor 12 from regenerator unit 30.

Figure 5:
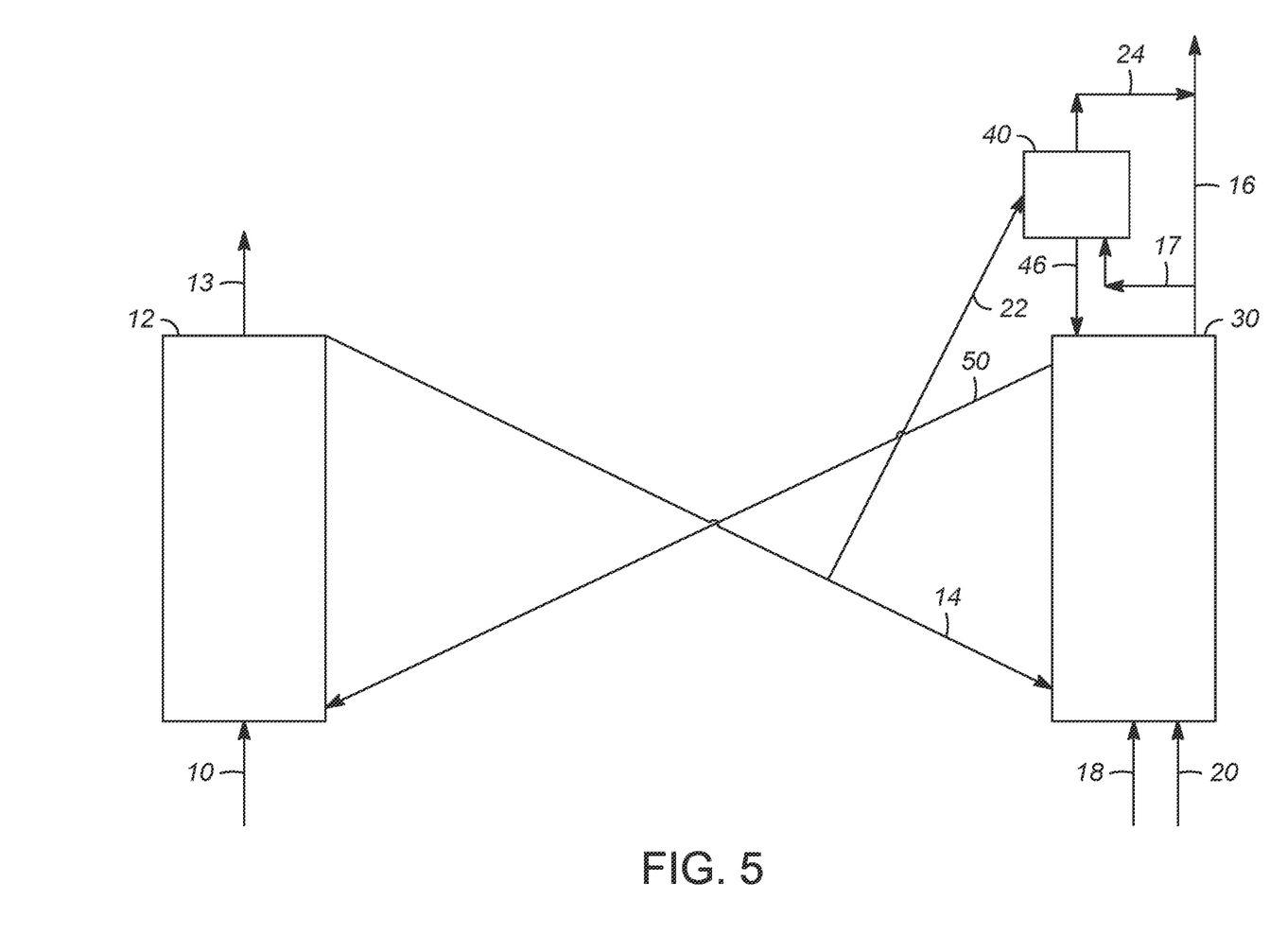
FIG. 5 is a schematic drawing of a process and apparatus of an alternative embodiment of the present disclosure in which the rejuvenation unit is above the regeneration unit.

FIG. 5 shows a variation of the invention where the rejuvenator 40 is above the regenerator unit 30. A PDH reactor 12 is shown in FIG. 1. A feed line 10 may deliver a reactant stream of feed to the reactor 12. The reactant stream may predominantly comprise propane or butane, but other paraffins such as ethane may be present in the reactant stream in conjunction with or to the exclusion of other paraffins. Any feed distributor can distribute the reactant stream to the reactor 12. A product stream 13 such as a mixture of propylene and hydrogen exits a top portion of reactor 12. Spent catalyst stream 14 is removed from the reactor 12 and sent to the bottom of regenerator unit 30. A small portion 22 (about 0.05-5% in quantity) of spent catalyst 14 is removed and sent to a catalyst rejuvenator unit 40 which is heated indirectly by a portion 17 of hot flue gas from regenerator unit 30, for instance using a heat exchanger to exchange heat between the flue gas and the catalyst. A flue gas stream 24 is combined into flue gas stream 16. The rejuvenated catalyst exits the bottom of rejuvenator 40 and is sent to regenerator 30 through pipe 46. In connection with regenerator 30 is shown a regeneration flue gas 16 exiting out the top, a regeneration gas stream 18 and a fuel stream 20 such as a fuel gas entering the bottom of regenerator 30. Regenerated catalyst stream 50 is returned to reactor 12 from regenerator unit 30.

Figure 6:
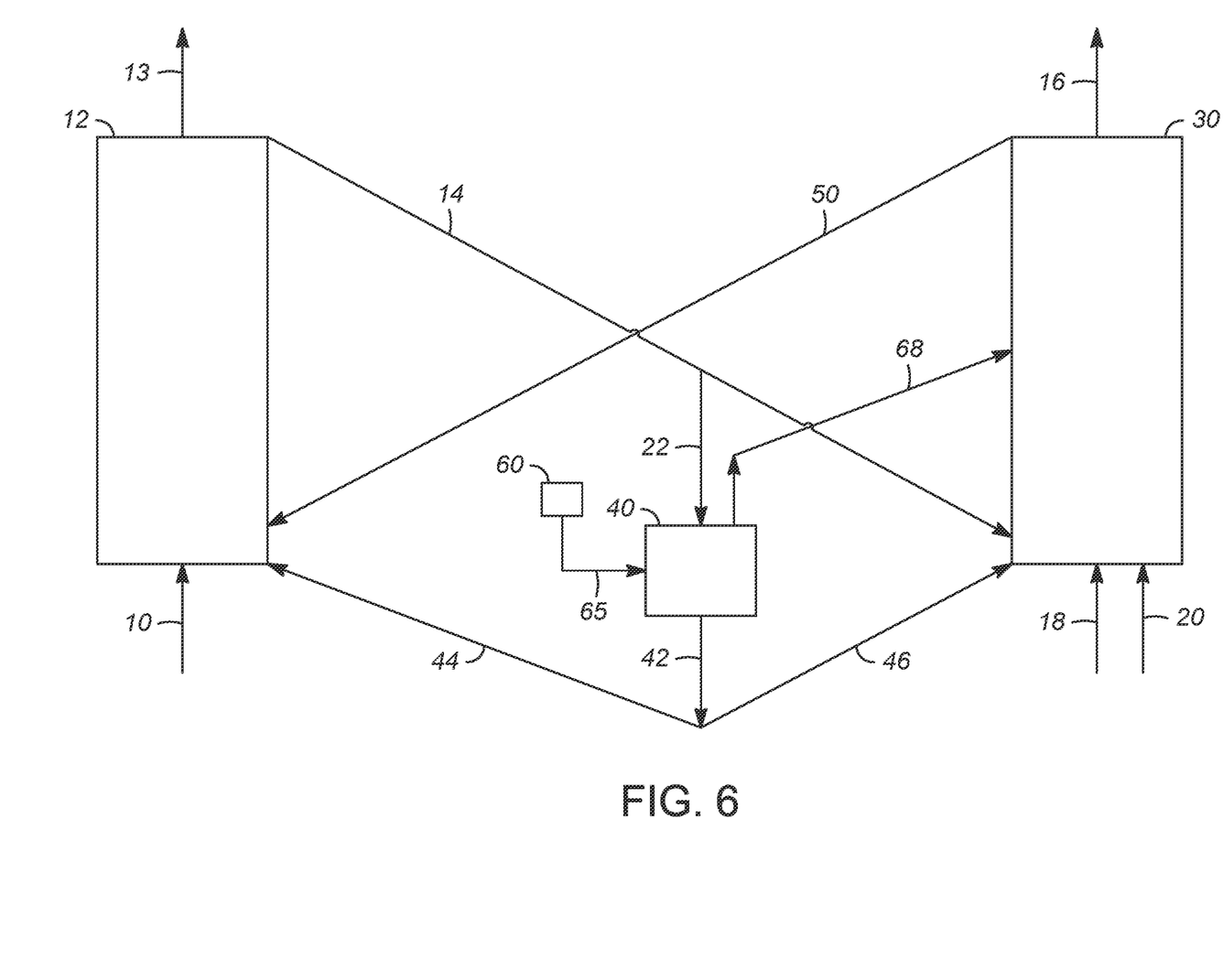
FIG. 6 is a schematic drawing of a process and apparatus of an embodiment in which hot air is sent to the catalyst rejuvenator.

In another embodiment, air is heated externally and used to heat the catalyst in the rejuvenator. A reactor 12 is shown in FIG. 6. A feed line 10 may deliver a reactant stream of feed such as propane to the reactor 12. The reactant stream may predominantly comprise propane or butane, but other paraffins such as ethane may be present in the reactant stream in conjunction with or to the exclusion of other paraffins. Any suitable feed distributor can distribute the reactant stream to the reactor 12. A product stream 13 such as a mixture of propylene and hydrogen exits a top portion of reactor 12. Spent catalyst stream 14 is removed from the reactor 12 and sent to the bottom of regenerator unit 30. A small portion 22 (about 0.05-5% in quantity) of spent catalyst 14 is removed and sent to a catalyst rejuvenator unit 40. A heater 60 is used to heat a stream of air 65. The heater 60 may be an electric heater, a fired heater or any heater capable of heating flowing air. The air is heated to a temperature above the desired rejuvenation temperature, for instance the air may be heated to 850-1000° C. The stream of hot air 65 is directed to the rejuvenator 40. In the rejuvenator, the catalyst is heated by the stream of hot air 65. After contacting the catalyst, the air has transferred some heat to the catalyst and is directed to the regenerator 30 through pipe 68, or may be vented separately. The rejuvenated catalyst 42 exits the bottom of rejuvenator 40 and either returns to reactor 12 through pipe 44 or is sent to regenerator 30 through pipe 46. In connection with regenerator 30 is shown a regeneration flue gas 16 exiting out the top, a regeneration gas stream 18 and a fuel stream 20 such as a fuel gas entering the bottom of regenerator 30. Regenerated catalyst stream 50 is returned to reactor 12 from regenerator unit 30.

The dehydrogenation catalyst may be of any of a variety of catalysts suitable for a fluidized bed dehydrogenation unit. The dehydrogenation catalyst selected should minimize cracking reactions and favor dehydrogenation reactions. Suitable catalysts for use herein include an active metal which may be dispersed in a porous inorganic carrier material such as silica, alumina, silica alumina, zirconia, or clay. An exemplary embodiment of a catalyst includes alumina or silica-alumina containing gallium, a noble metal, and an alkali or alkaline earth metal. In most cases, the catalyst contains gallium.

The catalyst support comprises a carrier material, a binder and an optional filler material to provide physical strength and integrity. The carrier material may include alumina or silica-alumina. Silica sol or alumina sol or other sources may be used as the binder precursor. The alumina or silica-alumina generally contains alumina of gamma, theta and/or delta phases. The catalyst support particles may have a nominal diameter of about 20 to about 200 micrometers with the average diameter of about 50 to about 150 micrometers. Preferably, the surface area of the catalyst support is 85-140 m$^2$/g.

The dehydrogenation catalyst may support a dehydrogenation metal. The dehydrogenation metal may be a one or a combination of transition metals. A noble metal may be a preferred dehydrogenation metal such as platinum or palladium. Gallium is an effective supporting metal for paraffin dehydrogenation. Metals may be deposited on the catalyst support by impregnation or other suitable methods or included in the carrier material or binder during catalyst preparation.

The acid function of the catalyst should be minimized to prevent cracking and favor dehydrogenation. Alkali metals and alkaline earth metals may also be included in the catalyst to attenuate the acidity of the catalyst. Rare earth metals may be included in the catalyst to control the activity of the catalyst. Concentrations of 0.001% to 10 wt % metals may be incorporated into the catalyst. In the case of the noble metals, it is preferred to use about 10 parts per million (ppm) by weight to about 600 ppm by weight noble metal. More preferably it is preferred to use 10-100 ppm by weight noble metal. The preferred noble metal is platinum. Gallium should be present in the range of 0.3 wt % to about 3 wt %, preferably about 0.5 wt % to about 2 wt %. Alkali and alkaline earth metals are present in the range of about 0.05 wt % to about 1 wt %. The stripped, spent dehydrogenation catalyst is transported by the spent catalyst pipe to the regenerator to combust the coke on the spent catalyst and regenerate the spent catalyst into regenerated catalyst. An oxygen supply gas is provided which lifts the spent catalyst in a combustion chamber through a catalyst separator and into a separation chamber. The coke is burned off the spent catalyst by contact with the oxygen supply gas at regeneration conditions. In an exemplary embodiment, air is used as the oxygen supply gas, because air is readily available and provides sufficient oxygen for combustion. Exemplary regeneration conditions include a temperature from about 500° C. (900° F.) to about 900° C. (1700° F.), preferably from about 670° C. to about 750° C., and a pressure of about 103 kPa (abs) (15 psia) to about 450 kPa (abs) (70 psia) in the regenerator. Hydrocarbon fuel may be added to the regenerator to boost the heat generated in the regenerator and help to provide heat in the reactor.

The embodiments herein provide a process and apparatus for contacting a reactant stream with fluidized catalyst and providing catalyst regeneration and rejuvenation to maintain catalyst activity.

EXAMPLES

Example 1

Catalyst was prepared by incipient wetness impregnation of an aqueous solution of gallium nitrate, potassium nitrate, and tetraamine platinum nitrate on a micro-spheroidal spray dried alumina containing 1% $SiO_2$. The catalyst support had BET surface area of 134 $m^2$/g measured by nitrogen adsorption. Impregnation was followed by calcination in air for 4 hours at 750 C. Catalyst contained 0.0076% Pt, 1.56% Ga, 0.26% K, 0.5% Si (by weight) as measured by inductively charged plasma atomic emission spectroscopy (ICP-AES). Catalyst appearance was white. Carbon and nitrogen content were measured by CHN method D5291. Carbon content of the fresh catalyst was 0.07 wt %, close to the detection limit of 0.05 wt % (likely due to adsorbed carbonates). Nitrogen was not detectable (detection limit 0.05 wt %).

Long-term aging of catalyst was simulated by cycling the catalyst between reactor and regenerator conditions as follows:

Startup: 2 $cm^3$ of catalyst was loaded in a quartz tube reactor. Catalyst was heated to 120° C. in nitrogen and held 30 minutes. Temperature was increased to 720° C. in nitrogen at 10° C./min and regeneration conditions were initiated.

Regeneration step: Temperature was increased to 720° C. in nitrogen at 10° C./min. Gas composition was changed from nitrogen to 5% O2, 24.2% $H_2O$, balance $N_2$ (by volume) and was flowed for 2 minutes with gas flow rate of 15 standard $cm^3$ per minute per $cm^3$ of catalyst. Gas composition was changed back to nitrogen, temperature was held for 0.5 min, and cooling was initiated.

Reaction step: Sample was cooled to 620° C. in nitrogen at 13° C./min. Gas composition was changed from nitrogen to propane. Propane was flowed for 2 minutes with gas flow rate of 7.5 $cm^3$ per minute per $cm^3$ of catalyst. Gas composition was changed back to nitrogen, temperature was held for 0.5 min, and heating for regeneration step was initiated.

Additional cycles of regeneration-reaction were completed as indicated in the examples that follow (and in table 1), with an additional regeneration at the end of the program. Catalyst was cooled in nitrogen and unloaded for further testing.

Example 2

200 mg of catalyst from Example 1 which was cycle-aged for 315 cycles was loaded between quartz wool plugs in a quartz tube reactor with inner diameter 3.85 mm. Inert alpha alumina spheres were loaded below the catalyst bed to minimize thermal cracking. The reactor effluent composition was analyzed by transmission infrared spectroscopy which identified propane, propene, ethane, ethene, and methane products with data collection approximately every 7 sec. The effluent of the infrared analyzer was directed to a gas chromatograph which was used to occasionally analyze the product stream and check the accuracy of the infrared analyzer on the real product stream.

Catalyst was dried in nitrogen and held for 30 minutes at 120° C., then heated to 720° C. in nitrogen. The catalyst was then exposed to a mixture of dry gas consisting of 9 mol % $O_2$, 14 mole % $CO_2$, with the balance nitrogen, where the dry gas flow ($O_2$+$CO_2$+nitrogen) was 20 standard $cm^3$/min, mixed with 25 mole % steam generated by vaporizing water which was fed from a pump. Exposure to this steam/$O_2$/$CO_2$/nitrogen mixture was sustained for 1 minute, at which point it was discontinued and replaced with dry nitrogen.

After this pretreatment, the catalyst was cooled to 620° C. in dry nitrogen. The catalyst was then exposed to 2 mol % $H_2O$ in nitrogen, generated by bubbling nitrogen through a saturator in a temperature-controlled bath. The wet pretreatment of the catalyst was maintained for 60 minutes. The nitrogen/$H_2O$ mixture was then stopped and replaced with 9 standard $cm^3$/min of propane and 1.5 standard $cm^3$/min of hydrogen feed. Feed was flowed for 2 minutes, after which gas composition was switched to nitrogen. The first exposure to propane in the catalyst test is denoted as testing cycle 1 in Table 1. The temperature was increased to 720° C. for regeneration. During regeneration, the catalyst was then exposed to a mixture of dry gas consisting of 9 mol % $O_2$, 14 mol % $CO_2$, with the balance nitrogen, where the dry gas flow ($O_2$+$CO_2$+nitrogen) was 20 standard $cm^3$/min, mixed with 25 mol % steam generated by vaporizing water which was fed from a pump. Exposure to this steam/$O_2$/$CO_2$/nitrogen mixture was sustained for 1 minute, at which point it was discontinued and replaced with dry nitrogen. The catalyst was then cooled to the next reaction step. The $O_2$/propane cycles were repeated four times. The propane conversion at or near 0.65 min on stream and at or near 1.42 min on stream is shown in Table 1.

Example 3

Same as Example 2 except 945 cycles of aging were completed prior to testing. Also, in the first two cycles the feed blend was 9 standard cm$^3$/min of propane, 1.5 standard cm$^3$/min of hydrogen and also included 1.0 standard cm$^3$/min of nitrogen. In the third and fourth cycles, the feed blend was the same as the first two cycles but also included 8 mol ppm of H$_2$S. H$_2$S was added by using an N$_2$/H$_2$S blend which was mixed with the feed stream downstream of the water saturator. The propane conversion at or near 0.65 min on stream and at or near 1.42 min on stream in each cycle is shown in Table 1.

Example 4

Same as Example 2 except 1576 cycles of aging were completed prior to testing. Also, the pretreatment and regeneration dry gas used during testing cycles was 7 standard cm$^3$/min of 5 mole % O$_2$, 8.1% CO$_2$. Also, 8 cycles were completed in total. In the 5$^{th}$ and 6$^{th}$ cycles, the feed blend was 9 standard cm$^3$/min of propane, 1.5 standard cm$^3$/min of hydrogen and also included 1.0 standard cm$^3$/min of nitrogen. In the 7th and 8th cycles, the feed blend was the same as the first two cycles but also included 8 mol ppm of H$_2$S. H$_2$S was added by using an N$_2$/H$_2$S blend which was mixed with the feed stream downstream of the water saturator. The propane conversion at or near 0.65 min on stream and at or near 1.42 min on stream in each cycle is shown in Table 1.

Example 5

Same as Example 2 except 3781 cycles of aging were completed prior to testing with the following differences: The pretreatment and regeneration dry gas used during the first four testing cycles was 7 standard cm$^3$/min of 5 mole % O$_2$, 8.1% CO$_2$. After the first four cycles, additional cycles were completed. In the regeneration portion of cycles 5-8, the same gas composition and conditions were used as in example 2. In the 5$^{th}$ and 6$^{th}$ cycles, the feed blend was 9 standard cm$^3$/min of propane, 1.5 standard cm$^3$/min of hydrogen and also included 1.0 standard cm$^3$/min of nitrogen. In the 7th and 8th cycles, the feed blend was the same as the first two cycles but also included 8 mol ppm of H$_2$S. H$_2$S was added by using an N$_2$/H$_2$S blend which was mixed with the feed stream downstream of the water saturator. The propane conversion at or near 0.65 min on stream and at or near 1.42 min on stream in each cycle is shown in Table 1.

Example 6

Same as Example 2 except 4411 cycles of aging were completed prior to testing, with the following differences: The propane containing feed blend was 9 standard cm$^3$/min of propane, 1.5 standard cm$^3$/min of hydrogen and also included 1.0 standard cm$^3$/min of nitrogen. In the 3rd and 4th cycles, the feed blend was the same as the first two cycles but also included 8 mol ppm of H$_2$S. H$_2$S was added by using an N$_2$/H$_2$S blend which was mixed with the feed stream downstream of the water saturator. The propane conversion at or near 0.65 min on stream and at or near 1.42 min on stream in each cycle is shown in After thousands of regeneration/reaction cycles, catalyst activity clearly decreased.

TABLE 1

| Example | Number of aging cycles | Testing Cycle | H$_2$S ppm | Data from time on stream (min) | Propane conversion (mol %) | Data from time on stream (min) | Propane conversion (mol %) |
|---|---|---|---|---|---|---|---|
| 2 | 315 | 1 | 0 | 0.54, 0.76[a] | 48.6, 47.8 | 1.42 | 46.3 |
| 2 | 315 | 2 | 0 | 0.65 | 48.1 | 1.42 | 46.4 |
| 2 | 315 | 3 | 0 | 0.54, 0.76[a] | 48.7, 47.9 | 1.42 | 46.0 |
| 2 | 315 | 4 | 0 | 0.65 | 47.9 | 1.30, 1.53[b] | 46.6, 46.1 |
| 3 | 945 | 1 | 0 | 0.54, 0.76[a] | 43.9, 44.3 | 1.42 | 41.9 |
| 3 | 945 | 2 | 0 | 0.54, 0.76[a] | 44.0, 43.6 | 1.42 | 41.1 |
| 3 | 945 | 3 | 8 | 0.65 | 42.9 | 1.30, 1.53[b] | 39.4, 36.6 |
| 3 | 945 | 4 | 8 | 0.65 | 43.5 | 1.42 | 37.0 |
| 4 | 1576 | 1 | 0 | 0.54, 0.76[a] | 41.2, 41.0 | 1.42 | 36.9 |
| 4 | 1576 | 2 | 0 | 0.65 | 41.2 | 1.30, 1.53[b] | 37.9, 38.5 |
| 4 | 1576 | 3 | 0 | 0.65 | 41.7 | 1.42 | 37.8 |
| 4 | 1576 | 4 | 0 | 0.65 | 42.2 | 1.42 | 37.7 |
| 4 | 1576 | 1 | 0 | 0.65 | 40.2 | 1.30, 1.53[b] | 36.7, 36.3 |
| 4 | 1576 | 2 | 0 | 0.65 | 40.0 | 1.30, 1.53[b] | 36.6, 36.2 |
| 4 | 1576 | 3 | 8 | 0.65 | 37.5 | 1.30, 1.53[b] | 32.8, 30.9 |
| 4 | 1576 | 4 | 8 | 0.54, 0.76[a] | 39.0, 35.9 | 1.42 | 31.8 |
| 5 | 3781 | 1 | 0 | 0.65 | 24.84 | 1.42 | 21.1 |
| 5 | 3781 | 2 | 0 | 0.54, 0.76[a] | 23.7, 23.5 | 1.42 | 20.9 |
| 5 | 3781 | 3 | 0 | 0.65 | 23.0 | 1.42 | 21.4 |
| 5 | 3781 | 4 | 0 | 0.65 | 23.1 | 1.42 | 21.4 |
| 5 | 3781 | 5 | 0 | 0.54, 0.76[a] | 21.6, 21.1 | 1.42 | 19.0 |
| 5 | 3781 | 6 | 0 | 0.54, 0.76[a] | 21.7, 20.9 | 1.42 | 19.0 |
| 5 | 3781 | 7 | 8 | 0.65 | 21.5 | 1.42 | 18.2 |
| 5 | 3781 | 8 | 8 | 0.65 | 21.8 | 1.30, 1.53[b] | 18.8, 18.6 |
| 6 | 4411 | 1 | 0 | 0.65 | 22.0 | 1.30, 1.53[b] | 21.5, 20.8 |
| 6 | 4411 | 2 | 0 | 0.54, 0.76[a] | 23.3, 22.8 | 1.42 | 22.5 |
| 6 | 4411 | 3 | 8 | 0.54, 0.76[a] | 20.6, 19.5 | 1.42 | 18.1 |
| 6 | 4411 | 4 | 8 | 0.65 | 20.5 | 1.30, 1.53[b] | 18.5, 18.2 |

[a]No datapoint at 0.65 min. Data is reported for 0.54 min and 0.76 min.
[b]No datapoint at 1.42 min. Data is reported for 1.30 min and 1.53 min.

Example 7

After completion of example 5, the same loading of cycled catalyst was subjected to four more regeneration/reaction cycles, but now with longer exposure time: The temperature was increased to 720° C. for regeneration. During regeneration, the catalyst was then exposed to a mixture of dry gas consisting of 9 mole % $O_2$, 14 mole % $CO_2$, with the balance nitrogen, where the dry gas flow ($O_2$+$CO_2$+nitrogen) was 20 standard cm$^3$/min, mixed with 25 mole % steam generated by vaporizing water which was fed from a pump. Exposure to this steam/$O_2$/$CO_2$/nitrogen mixture was sustained for 5 minutes, at which point it was discontinued and replaced with dry nitrogen. The catalyst was then cooled to 620° C. for the reaction step. The catalyst was then exposed to 2 mol % $H_2O$ in nitrogen, generated by bubbling nitrogen through a saturator in a temperature-controlled bath. The wet pre-treatment of the catalyst was maintained for 60 minutes. The nitrogen/$H_2O$ mixture was then stopped and replaced with 9 standard cm$^3$/min of propane and 1.5 standard cm$^3$/min of hydrogen feed. Feed was flowed for 2 minutes, after which gas composition was switched to nitrogen. This exposure to propane in the catalyst test is denoted as testing cycle 9 in table 2. The temperature was increased to 720° C. for the next regeneration. Cycles 10, 11, and 12 were identical to cycle 9 except for the duration of exposure to the steam/$O_2$/$CO_2$/nitrogen mixture. Regeneration in cycle 10 was also 5 minutes while in cycles 11 and 12, the catalyst was held in the flowing regeneration gas mixture for 60 minutes. The propane conversion at or near 0.65 min on stream and at or near 1.42 min on stream in each cycle is shown in Table 2.

TABLE 2

| Ex. | Number of aging cycles | Testing Cycle | Regeneration time (min) | H2S ppm | Data from time on stream (min) | Propane conversion (mol %) | Data from time on stream (min) | Propane conversion (mol %) |
|---|---|---|---|---|---|---|---|---|
| 7 | 3781 | 9 | 5 | 0 | 0.65 | 31.4 | 1.30, 1.53[b] | 28.5, 28.3 |
| 7 | 3781 | 10 | 5 | 0 | 0.65 | 35.6 | 1.42 | 32.9 |
| 7 | 3781 | 11 | 60 | 0 | 0.65 | 45.9 | 1.30, 1.53[b] | 46.4, 46.8 |
| 7 | 3781 | 12 | 60 | 0 | 0.54, 0.76[a] | 46.4, 46.8 | 1.42 | 40.1 |

[a]No datapoint at 0.65 min. Data is reported for 0.54 min and 0.76 min.
[b]No datapoint at 1.42 min. Data is reported for 1.30 min and 1.53 min.

Example 8

After completion of example 7, the same loading of cycled catalyst was then subjected to four more regeneration/reaction cycles with long regeneration, but now with higher $O_2$ content in the regeneration gas: The temperature was increased to 720° C. for regeneration. During regeneration, the catalyst was then exposed to a mixture of dry gas consisting of 20 mol % O2, 32 mol % $CO_2$, with the balance nitrogen, where the dry gas flow ($O_2$+$CO_2$+nitrogen) was 19 standard cm3/min, mixed with 25 mol % steam generated by vaporizing water which was fed from a pump. Exposure to this steam/$O_2$/$CO_2$/nitrogen mixture was sustained for 5 minutes, at which point it was discontinued and replaced with dry nitrogen. The catalyst was then cooled to 620° C. for the reaction step. The catalyst was then exposed to 2 mol % $H_2O$ in nitrogen, generated by bubbling nitrogen through a saturator in a temperature-controlled bath. The wet pre-treatment of the catalyst was maintained for 60 minutes. The nitrogen/$H_2O$ mixture was then stopped and replaced with 9 standard cm$^3$/min of propane and 1.5 standard cm$^3$/min of hydrogen feed. Feed was flowed for 2 minutes, after which gas composition was switched to nitrogen. This exposure to propane in the catalyst test is denoted as testing cycle 13 in table 3. The temperature was increased to 720° C. for the next regeneration. Cycles 14, 15, and 16 were identical to cycle 13 except for the duration of exposure to the steam/$O_2$/$CO_2$/nitrogen mixture. Regeneration in cycle 14 was also 5 minutes while in cycles 15 and 16, the catalyst was held in the flowing regeneration gas mixture for 60 minutes. The propane conversion at or near 0.65 min on stream and at or near 1.42 min on stream in each cycle is shown in Table 3. At least on an already rejuvenated catalyst, 9 and 20 mol % $O_2$ have similar effect on catalyst activity.

Example 9

After completion of example 6, the same loading of cycled catalyst was then subjected to more regeneration/reaction cycles with higher $O_2$ content in the regeneration gas, and for various times: The temperature was increased to 720° C. for regeneration. During regeneration, the catalyst was then exposed to a mixture of dry gas consisting of 20 mol % $O_2$, 32 mole % $CO_2$, with the balance nitrogen, where the dry gas flow (02+$CO_2$+nitrogen) was 19 standard cm$^3$/min, mixed with 25 mole % steam generated by vaporizing water which was fed from a pump. Exposure to this steam/$O_2$/$CO_2$/nitrogen mixture was sustained 0.5, 1, 2, 3, or 5 min as indicated in Table 3, at which point it was discontinued and replaced with dry nitrogen. The catalyst was then cooled to 620° C. for the reaction step. The catalyst was then exposed to 2 mol % $H_2O$ in nitrogen, generated by bubbling nitrogen through a saturator in a temperature-controlled bath. The wet pre-treatment of the catalyst was maintained for 60 minutes. The nitrogen/$H_2O$ mixture was then stopped and replaced with 9 standard cm$^3$/min of propane and 1.5 standard cm$^3$/min of hydrogen feed. Feed was flowed for 2 minutes, after which gas composition was switched to nitrogen. The temperature was increased to 720° C. for the next regeneration. The propane conversion at or near 0.65 min on stream and at or near 1.42 min on stream in each cycle is shown in Table 3. Recovery of catalyst activity in 20% O2 depends on the duration of treatment.

After these cycles, 4 additional cycles (#17-20) were completed with lower % O2 and 1 min duration. During regeneration preceding these cycles, the catalyst was exposed to a mixture of dry gas consisting of 9 mol % $O_2$, 14 mol % $CO_2$, with the balance nitrogen, where the dry gas flow ($O_2$+$CO_2$+nitrogen) was 20 standard cm$^3$/min, mixed with 25 mol % steam generated by vaporizing water which was fed from a pump. Exposure to this steam/$O_2$/$CO_2$/nitrogen mixture was sustained for 1 minute, at which point it was discontinued and replaced with dry nitrogen. After this regeneration treatment, the catalyst was cooled to 620° C. in dry nitrogen. The catalyst was then exposed to 2 mol % $H_2O$ in nitrogen, generated by bubbling nitrogen through a saturator in a temperature-controlled bath. The wet pretreatment of the catalyst was maintained for 60 minutes. The nitrogen/$H_2O$ mixture was then stopped and replaced with 9 standard $cm^3$/min of propane and 1.5 standard $cm^3$/min of hydrogen feed. Feed was flowed for 2 minutes, after which gas composition was switched to nitrogen. The data from these cycles is also shown in table 3. Catalyst maintains activity after through 4 cycles after rejuvenation treatments.

Example 11

In this example a catalyst had composition of 1 wt % $SiO2$, 1.2 wt % Ga, 45 wppm Pt and 0.25 wt % K and an alumina support. The catalyst was cycled 3546 times using the conditions for long term simulated cycling described in example 1. 200 mg of catalyst was loaded between quartz wool plugs in a quartz tube reactor with inner diameter 3.85 mm. Inert alpha alumina spheres were loaded below the

TABLE 3

| Ex. | Number of aging cycles | Testing Cycle | Regeneration time (min) | % O2 in dry gas | Data from time on stream (min) | Propane conversion (mol %) | Data from time on stream (min) | Propane conversion (mol %) |
|---|---|---|---|---|---|---|---|---|
| 8 | 3781 | 13 | 5 | 20 | 0.65 | 46.3 | 1.42 | 38.7 |
| 8 | 3781 | 14 | 5 | 20 | 0.65 | 46.0 | 1.42 | 38.7 |
| 8 | 3781 | 15 | 60 | 20 | 0.54, 0.76[a] | 45.9, 42.9 | 1.42 | 34.3 |
| 8 | 3781 | 16 | 60 | 20 | 0.54, 0.76[a] | 44.8, 42.3 | 1.42 | 31.6 |
| 9 | 4411 | 5 | 0.5 | 20 | 0.54, 0.76[a] | 26.0, 24.8 | 1.30, 1.53[b] | 24.0 |
| 9 | 4411 | 6 | 0.5 | 20 | 0.54, 0.76[a] | 27.0, 26.8 | 1.42 | 25.1 |
| 9 | 4411 | 7 | 1 | 20 | 0.65 | 28.7 | 1.30, 1.53[b] | 27.9, 27.4 |
| 9 | 4411 | 8 | 1 | 20 | 0.65 | 32.5 | 1.42 | 28.8 |
| 9 | 4411 | 9 | 1 | 20 | 0.54, 0.76[a] | 33.5, 32.5 | 1.42 | 30.4 |
| 9 | 4411 | 10 | 2 | 20 | 0.54, 0.76[a] | 35.4, 35.6 | 1.42 | 33.9 |
| 9 | 4411 | 11 | 2 | 20 | 0.54, 0.76[a] | 38.2, 38.6 | 1.42 | 35.7 |
| 9 | 4411 | 12 | 0.5 | 20 | 0.54, 0.76[a] | 38.4, 37.7 | 1.42 | 36.3 |
| 9 | 4411 | 13 | 3 | 20 | 0.65 | 39.7 | 1.30, 1.53[b] | 38.1, 37.3 |
| 9 | 4411 | 14 | 3 | 20 | 0.54, 0.76[a] | 42.2, 41.2 | 1.42 | 38.6 |
| 9 | 4411 | 15 | 5 | 20 | 0.54, 0.76[a] | 44.3, 43.8 | 1.42 | 41.7 |
| 9 | 4411 | 16 | 5 | 20 | 0.65 | 46.1 | 1.42 | 42.5 |
| 9 | 4411 | 17 | 1 | 9 | 0.65 | 45.5 | 1.42 | 42.7 |
| 9 | 4411 | 18 | 1 | 9 | 0.65 | 45.4 | 1.30, 1.53[b] | 42.8, 41.7 |
| 9 | 4411 | 19 | 1 | 9 | 0.65 | 45.6 | 1.42 | 42.5 |
| 9 | 4411 | 20 | 1 | 9 | 0.54, 0.76[a] | 45.1, 44.9 | 1.42 | 42.9 |

[a]No datapoint at 0.65 min. Data is reported for 0.54 min and 0.76 min.
[b]No datapoint at 1.42 min. Data is reported for 1.30 min and 1.53 min.

Example 10

The same catalyst that had been tested in example 2 after 315 cycles was tested again (but a fresh loading of the catalyst was used that had yet been subjected to testing). The catalyst was tested with the same conditions as were used in example 8 in order to determine if the recoverable activity obtained in example 8 on a catalyst cycled 3871 times after long exposure to 20% O2 is the same obtainable activity on a catalyst cycled only 315 times. The propane conversion at or near 0.65 min on stream and at or near 1.42 min on stream in each cycle is shown in Table 4. Based on this result compared to example 8, the same performance is seen after long rejuvenation treatment to recover activity on a catalyst cycled 315 times as on a catalyst cycled 3871 times.

catalyst bed to minimize thermal cracking. The reactor effluent composition was analyzed by transmission infrared spectroscopy which identified propane, propene, ethane, ethene, and methane products with data collection approximately every 7 sec. The effluent of the infrared analyzer was directed to a gas chromatograph which was used to occasionally analyze the product stream and check the accuracy of the infrared analyzer on the real product stream.

Catalyst was dried in nitrogen and held for 30 minutes at 120° C., then heated to 720° C. in nitrogen. The catalyst was then exposed to a mixture of dry gas consisting of 9 mol % $O_2$, 14 mole % $CO_2$, with the balance nitrogen, where the dry gas flow ($O_2$+$CO_2$+nitrogen) was 20 standard $cm^3$/min, mixed with 25 mole % steam generated by vaporizing water which was fed from a pump. Exposure to this steam/$O_2$/

TABLE 4

| Ex. | Number of aging cycles | Testing Cycle | Regeneration time (min) | H2S ppm | Data from time on stream (min) | Propane conversion (mol %) | Data from time on stream (min) | Propane conversion (mol %) |
|---|---|---|---|---|---|---|---|---|
| 10 | 315 | 1 | 5 | 0 | 0.65 | 48.6, 47.8 | 1.42 | 46.3 |
| 10 | 315 | 2 | 5 | 0 | 0.65 | 48.1 | 1.42 | 46.4 |
| 10 | 315 | 3 | 60 | 0 | 0.54, 0.76[a] | 48.7, 47.9 | 1.42 | 46.0 |
| 10 | 315 | 4 | 60 | 0 | 0.65 | 47.9 | 1.30, 1.53[b] | 46.6, 46.1 |

[a]No datapoint at 0.65 min. Data is reported for 0.54 min and 0.76 min.
[b]No datapoint at 1.42 min. Data is reported for 1.30 min and 1.53 min.

$CO_2$/nitrogen mixture was sustained for 1 minute, at which point it was discontinued and replaced with dry nitrogen.

After this pretreatment, the catalyst was cooled to 620° C. in dry nitrogen. The catalyst was then exposed to 2 mol % $H_2O$ in nitrogen, generated by bubbling nitrogen through a saturator in a temperature-controlled bath. The wet pretreatment of the catalyst was maintained for 60 minutes. The nitrogen/$H_2O$ mixture was then stopped and replaced with 9 standard $cm^3$/min of propane, 1 standard $cm^3$/min of nitrogen, and 1.5 standard $cm^3$/min of hydrogen feed. Feed was flowed for 2 minutes, after which gas composition was switched to nitrogen. The first exposure to propane in the catalyst test is denoted as testing cycle 1 in Table 1. The temperature was increased to 720° C. for regeneration. During regeneration, the catalyst was then exposed to a mixture of dry gas consisting of 9 mol % $O_2$, 14 mol % $CO_2$, with the balance nitrogen, where the dry gas flow ($O_2$+$CO_2$+nitrogen) was 20 standard $cm^3$/min, mixed with 25 mol % steam generated by vaporizing water which was fed from a pump. Exposure to this steam/$O_2$/$CO_2$/nitrogen mixture was sustained for 1 minute, at which point it was discontinued and replaced with dry nitrogen. The catalyst was then cooled to the next reaction step. 7 cycles were completed using this regeneration program. In cycles 3 and 4, the feed during exposure to propane also included 8 mol ppm of $H_2S$. The propane conversion at or near 0.65 min on stream and at or near 1.42 min on stream is shown in Table 5.

Preceding the next (8$^{th}$) cycle, the catalyst was rejuvenated by replacing the regeneration step exposing the catalyst to 20 mol % O2/80% $N_2$ for 40 minutes at 750° C. As shown in table 5, this hotter, longer, treatment simulating rejuvenation in hot air results in recovery of significant activity. Furthermore, this activity is maintained for many cycles, even after returning to a milder, shorter regeneration condition. Following the 8$^{th}$ cycle, all cycles had a regeneration step consisting of regeneration for 1 min at 720 C with dry gas composition of 6.25% mol % O2+9.7 mol % CO2, with 25 mol % steam. Cycling was continued for total of 22 cycles (14 after rejuvenation) to demonstrate that activity is maintained. The propane conversion in each cycle at or near 0.65 min on stream and at or near 1.42 min on stream is shown in Table 5.

TABLE 5

| Ex. | Number of aging cycles | Testing Cycle | Regeneration time (min), temp (C.), % O2 | H2S ppm | Data from time on stream (min) | Propane conversion (mol %) | Data from time on stream (min) | Propane conversion (mol %) |
|---|---|---|---|---|---|---|---|---|
| 11 | 3546 | 1 | 1, 720, 9% | 0 | 0.65 | 32.9 | 1.30, 1.53$^b$ | 31.1, 30.7 |
| 11 | 3546 | 2 | 1, 720, 9% | 0 | 0.65 | 34.4, 33.4 | 1.42 | 31.8 |
| 11 | 3546 | 3 | 1, 720, 9% | 8 | 0.54, 0.76$^a$ | 31.6, 29.2 | 1.42 | 25.3 |
| 11 | 3546 | 4 | 1, 720, 9% | 8 | 0.54, 0.76$^a$ | 30.7, 29.0 | 1.30, 1.53$^b$ | 25.1 |
| 11 | 3546 | 5 | 1, 720, 9% | 0 | 0.54, 0.76$^a$ | 33.5, 33.7 | 1.42 | 32.0 |
| 11 | 3546 | 6 | 1, 720, 9% | 0 | 0.65 | 34.4 | 1.42 | 32.2 |
| 11 | 3546 | 7 | 1, 720, 9% | 0 | 0.65 | 33.8 | 1.42 | 32.9 |
| 11 | 3546 | 8 | 40, 750, 20% | 0 | 0.65 | 44.2 | 1.42 | 34.3 |
| 11 | 3546 | 9 | 1, 720, 6.25% | 0 | 0.65 | 42.9 | 1.42 | 34.4 |
| 11 | 3546 | 10 | 1, 720, 6.25% | 0 | 0.65 | 43.9 | 1.42 | 34.1 |
| 11 | 3546 | 11 | 1, 720, 6.25% | 0 | 0.54, 0.76$^a$ | 44.0, 41.7 | 1.42 | 34.0 |
| 11 | 3546 | 12 | 1, 720, 6.25% | 0 | 0.65 | 42.7 | 1.42 | 33.1 |
| 11 | 3546 | 13 | 1, 720, 6.25% | 0 | 0.54, 0.76$^a$ | 43.3, 40.9 | 1.42 | 33.4 |
| 11 | 3546 | 14 | 1, 720, 6.25% | 0 | 0.65 | 41.9 | 1.30, 1.53$^b$ | 33.5, 32.9 |
| 11 | 3546 | 15 | 1, 720, 6.25% | 0 | 0.65 | 42.8 | 1.30, 1.53$^b$ | 35.2, 33.0 |
| 11 | 3546 | 16 | 1, 720, 6.25% | 0 | 0.54, 0.76$^a$ | 45.0, 42.2 | 1.42 | 35.4 |
| 11 | 3546 | 17 | 1, 720, 6.25% | 0 | 0.65 | 43.1 | 1.30, 1.53$^b$ | 35.7, 33.9 |
| 11 | 3546 | 18 | 1, 720, 6.25% | 0 | 0.54, 0.76$^a$ | 44.0, 41.6 | 1.42 | 34.2 |
| 11 | 3546 | 19 | 1, 720, 6.25% | 0 | 0.54, 0.76$^a$ | 44.6, 41.3 | 1.42 | 34.3 |
| 11 | 3546 | 20 | 1, 720, 6.25% | 0 | 0.65 | 42.6 | 1.30, 1.53$^b$ | 34.6, 33.5 |
| 11 | 3546 | 21 | 1, 720, 6.25% | 0 | 0.65 | 42.8 | 1.42 | 33.9 |
| 11 | 3546 | 22 | 1, 720, 6.25% | 0 | 0.65 | 42.6 | 1.30, 1.53$^b$ | 35.4, 33.0 |

$^a$No datapoint at 0.65 min. Data is reported for 0.54 min and 0.76 min.
$^b$No datapoint at 1.42 min. Data is reported for 1.30 min and 1.53 min.

The invention claimed is:

1. A process for managing or controlling catalyst activity comprising sending about 0.05 to 5% of quantity of catalyst flow within a propane dehydrogenation system to a catalyst rejuvenation unit wherein said system comprises a reactor, a catalyst regeneration unit and said catalyst rejuvenation unit and catalyst piping to send catalyst to and from each of said reactor, said catalyst regeneration unit and said catalyst rejuvenation unit, wherein the catalyst sent to said rejuvenation unit is heated to a temperature above 715° C. in presence of a gas comprising more than 2 mol % O2.

2. The process of claim 1 wherein said catalyst rejuvenation unit receives spent catalyst from said reactor, treats said spent catalyst at a temperature of above 715-790° C. sufficient to increase activity of said spent catalyst and then returns a rejuvenated catalyst to said reactor or to said catalyst regeneration unit.

3. The process of claim 1 wherein said catalyst is sent to said catalyst rejuvenation unit about every 200 cycles to about every 4000 cycles, wherein a cycle comprises the weight averaged period of time wherein said catalyst passes from said reactor to said regenerator unit and back.

4. The process of claim 3 wherein an interval between cycles is from about 80 to about 700 hours.

5. The process of claim 1 wherein said rejuvenation unit contains about 0.2% to about 0.6% of quantity of catalyst compared to said regeneration unit.

6. The process of claim 1 wherein said catalyst sent to said catalyst rejuvenation unit is spent catalyst, partially regenerated catalyst or fully regenerated catalyst.

7. The process of claim 1 wherein said catalyst sent to said rejuvenation unit is heated for at least 5 minutes.

8. The process of claim 1 wherein said catalyst comprises platinum and gallium.

9. The process of claim 1 wherein said catalyst is fluidized with air within said catalyst rejuvenation unit and remains within said catalyst rejuvenation unit for from 5-60 minutes.

10. The process of claim 1 wherein said rejuvenation unit is positioned above said catalyst regeneration unit and wherein a stream of flue gas from said regeneration unit is sent to said rejuvenation unit.

11. The process of claim 1 wherein a slip stream of regenerated or partially regenerated catalyst is sent from an upper portion of said catalyst regeneration unit to said rejuvenation unit.

12. The process of claim 1 wherein said rejuvenation unit is heated by preheated air or flue gas having a temperature of about 850-1000° C.

13. The process of claim 12 wherein said preheated air or flue gas is at a weight ratio to catalyst of about 0.5-0.7.

14. The process of claim 1 wherein a fluidization velocity of about 1.5-3.5 ft/s is found in said rejuvenation unit.

15. The process of claim 1 wherein said rejuvenation unit is operated as a batch process or a continuous process.

* * * * *